US011369450B2

(12) United States Patent
Bernstein

(10) Patent No.: US 11,369,450 B2
(45) Date of Patent: Jun. 28, 2022

(54) INSTRUMENT DRAPE

(71) Applicant: Intuitive Surgical Operations, Inc., Sunnyvale, CA (US)

(72) Inventor: Nicholas Leo Bernstein, Cary, NC (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1288 days.

(21) Appl. No.: 15/600,477

(22) Filed: May 19, 2017

(65) Prior Publication Data

US 2017/0333147 A1 Nov. 23, 2017

Related U.S. Application Data

(60) Provisional application No. 62/339,706, filed on May 20, 2016.

(51) Int. Cl.
| | |
|---|---|
| *A61B 46/10* | (2016.01) |
| *A61B 50/30* | (2016.01) |
| *A61B 34/30* | (2016.01) |
| *A61B 50/00* | (2016.01) |
| *A61B 34/35* | (2016.01) |
| *A61B 17/34* | (2006.01) |

(Continued)

(52) U.S. Cl.
CPC .............. *A61B 46/10* (2016.02); *A61B 34/30* (2016.02); *A61B 50/30* (2016.02); *A61B 17/3421* (2013.01); *A61B 34/35* (2016.02); *A61B 90/40* (2016.02); *A61B 2017/00477* (2013.01); *A61B 2050/0066* (2016.02)

(58) Field of Classification Search
CPC ......... A61B 46/00; A61B 46/10; A61B 46/13; A61B 46/17; A61B 46/20; A61B 46/23; A61B 46/27; A61B 46/30; A61B 2046/201; A61B 2046/205; A61B 2046/234; A61B 2046/236; A61B 50/00; A61B 50/30; A61B 2050/0066; A61B 2050/0079; A61B 34/30; A61B 2034/301; A61B 2034/305; A61B 34/70; A61B 90/08; A61B 90/10
See application file for complete search history.

(56) References Cited

U.S. PATENT DOCUMENTS 5,433,221 A * 7/1995 Adair ..................... A61B 46/10
                                                  128/849
5,496,259 A * 3/1996 Perkins .............. A61B 1/00142
                                                  600/121

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Camtu T Nguyen
(74) *Attorney, Agent, or Firm* — Fish & Richardson P.C.

(57) ABSTRACT

A surgical drape for providing a localized instrument sterility barrier includes: a tube having a proximal end and a distal end, the tube defining an interior bore sized to receive an elongated shaft of a surgical instrument; and a port coupler at the distal end of the tube, the port coupler configured to couple the distal end of the tube to a surgical port through which the elongated shaft extends. The tube is collapsible to accommodate relative movement between the instrument and the surgical port during a surgical procedure.

13 Claims, 6 Drawing Sheets

(51) Int. Cl.
    *A61B 17/00*      (2006.01)
    *A61B 90/40*      (2016.01)

(56) References Cited

U.S. PATENT DOCUMENTS

| | | | |
|---|---|---|---|
| 6,123,080 A * | 9/2000 | Mohan | A61B 46/10 128/849 |
| 8,075,528 B2 | 12/2011 | Widenhouse et al. | |
| 8,485,970 B2 * | 7/2013 | Widenhouse | A61B 17/3462 600/201 |
| 8,647,261 B2 * | 2/2014 | Jaworek | A61M 25/0111 600/114 |
| 2006/0111611 A1 * | 5/2006 | Eizenfeld | A61B 1/00135 600/124 |
| 2010/0081871 A1 * | 4/2010 | Widenhouse | A61B 17/3462 600/104 |
| 2015/0094611 A1 * | 4/2015 | Farhadi | A61B 10/04 600/562 |
| 2016/0045099 A1 * | 2/2016 | Farhadi | A61B 1/00142 600/116 |
| 2017/0000361 A1 * | 1/2017 | Meyering | A61B 10/0045 |

* cited by examiner

INSTRUMENT DRAPE

CROSS REFERENCE TO RELATED APPLICATIONS

This application is a non-provisional of and claims priority to U.S. Provisional Patent Application No. 62/339,706, filed on May 20, 2016, the entire contents of which are hereby incorporated by reference.

TECHNICAL FIELD

This specification generally relates to surgical drapes for use with teleoperated robotic systems.

BACKGROUND

Minimally invasive medical techniques (e.g., laparoscopy) have been used to reduce the amount of extraneous tissue which may be damaged during diagnostic or surgical procedures, thereby reducing patient recovery time, discomfort, and deleterious side effects. Such techniques were traditionally performed manually via a surgeon manipulating various surgical instruments within the patient's body, but can now by implemented using teleoperated robotic systems that provide telepresence. Performing minimally invasive surgery with teleoperated robotic systems facilitates increased precision and range of motion in manipulating surgical instruments when compared to manual techniques, but also introduces new challenges. One such challenge is the need to erect a sterility barrier between certain non-sterile portions of the surgical system (e.g., portions housing the various motors, sensors, encoders, and electrical connections that cannot withstand a sterilization process) and the area immediately adjacent the patient. A prior solution to this particular challenge has been to cover the non-sterile portions of the system with a sterile drape, leaving a sterilized instrument to be manipulated by the system uncovered, so that it can be easily replaced by another instrument during a surgical procedure. Thus, the sterile field encompasses the entire area of the operating room adjacent the patient's body, excluding the covered portions of surgical system.

SUMMARY

One aspect of the present disclosure features a surgical drape for providing a localized instrument sterility barrier. The surgical drape includes: a tube having a proximal end and a distal end, the tube defining an interior bore sized to receive an elongated shaft of a surgical instrument; and a port coupler at the distal end of the tube, the port coupler configured to couple the distal end of the tube to a surgical port through which the elongated shaft extends. The tube is collapsible to accommodate relative movement between the instrument and the surgical port during a surgical procedure.

Another aspect of the present disclosure features a computer-assisted surgical system. The system includes: a robotically operable surgical manipulator with an instrument interface; a surgical instrument removably mounted to the manipulator; and a surgical drape forming a localized sterility barrier around a portion of the instrument (e.g., a shaft of the instrument). The instrument includes: a proximal base engaging the instrument interface for operation of the surgical instrument; an elongated shaft extending from the proximal base, the shaft having a distal end; and an end effector residing at the distal end of the shaft and operably coupled to the proximal base by the shaft. The surgical drape includes: a tube having a proximal end and a distal end, the tube residing around the shaft and coupled to the proximal base of the instrument; and a port coupler coupling the distal end of the tube to a surgical port through which the shaft extends. The tube is collapsible to accommodate relative movement between the instrument and the surgical port during a surgical procedure.

In some examples, the drape further includes a base coupler at the proximal end of the tube, the base coupler coupling the drape to the proximal base of the instrument. In some examples, the proximal base of the instrument includes a flange having a pattern of external screw threads, and the base coupler includes a rigid circular collar having a pattern of internal screw threads configured to releasably engage the external screw threads of the flange.

In some examples, the tube includes a sheet of film sufficiently flexible to reversibly collapse as the proximal base is moved relative to the surgical port by the manipulator. In some examples, the tube includes an accordion structure configured to reversibly collapse as the proximal base is moved relative to the surgical port by the manipulator. In some examples, the tube includes an impervious tube wall having an exterior surface and a sterile interior surface. In some examples, the tube is sufficiently stiff to inhibit distention by an insufflation gas released through the surgical port into the tube.

In some examples, the port coupler is configured to form a sterile seal with the surgical port. In some examples, the port coupler includes a self-sealing closure configured to seal an interior bore of the tube when the port coupler is detached from the surgical port. In some examples, the self-sealing closure includes a resilient sealing lip. In some examples, the sealing lip includes a pair of opposing hinges to facilitate opening of the self-sealing closure. In some examples, the self-sealing closure includes a magnetic element along a portion of the distal end of the tube.

In some examples, the base coupler, tube, and port coupler are configured to withstand a sterilization process, such as a gamma irradiation for packaging and initial use, and autoclaving if subsequent use is desired.

Yet another aspect of the present disclosure features a method of configuring a robotically operable surgical instrument for a surgical procedure. The method includes: attaching a first end of a collapsible tubular surgical drape to a proximal base of the surgical instrument; and attaching an opposite second end of the surgical drape to a surgical port, such that the surgical drape forms a sterility barrier extending from the base of the surgical instrument to the surgical port that is deformable as the instrument is advanced through a port entrance.

In some examples, attaching the first end of the surgical drape to the proximal instrument base includes releasably engaging a pattern of external screw threads on a flange of the base with a pattern of internal screw threads on a rigid circular collar of the first end. In some examples, attaching the second end of the surgical drape to the surgical port includes forming a sterile seal therebetween.

In some examples, the method further includes, after attaching the first end of the surgical drape, positioning the surgical drape to cover an instrument shaft by extending an accordion structure of the surgical drape along a length of the instrument shaft. In some examples, the method further includes, after attaching the first end of the surgical drape, positioning the surgical drape to cover an instrument shaft by locating a sterile interior surface of the tubular drape adjacent a length of the instrument shaft.

In some examples, the method further includes: detaching the second end from the surgical port; sealing the second end of the surgical drape to maintain a sterility barrier about the surgical instrument; and re-attaching the second end of the surgical drape to the surgical port. In some examples, sealing the second end includes operating a self-sealing closure. In some examples, the self-sealing closure includes a resilient sealing lip. In some examples, the sealing lip includes a pair of opposing hinges to facilitate opening of the self-sealing closure. In some examples, the self-sealing closure includes a magnetic element along a portion of the second end.

In some examples, the method further includes, detaching the second end from the surgical port; sterilizing the surgical instrument and the surgical drape, with the first end remaining attached to the proximal base; and attaching the second end to a different surgical port.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

One or more of the illustrated elements may be exaggerated to better show the features, process steps, and results. Like reference numbers and designations in the various drawings may indicate like elements.

DETAILED DESCRIPTION

One or more embodiments of the present disclosure relate to surgical drapes for use with teleoperated robotic systems. In particular, the surgical drapes described herein are designed to provide a localized sterility barrier covering certain portions of the surgical instrument (particularly the shaft) in order to shield the sterile instrument from the uncovered non-sterile portions of the surgical system—e.g., the manipulator that supports and controls the instrument. Thus, the surgical drapes of the present disclosure provide a distinct paradigm shift from conventional robotic surgical drapes by inverting and shrinking the sterile field to the area immediately surrounding the surgical instrument, compared to previous drapes designed to cover non-sterile portions of the surgical system (discussed above). Such inverted surgical drapes are associated with the realization that conventional drapes covering large portions of the surgical system are expensive, add complexity and time to setup procedures, and restrict air flow around the manipulator, which contributes to heat dissipation problems. The inverted drape approach is also associated with the further realization that conventional robotic surgical drapes establish a very large sterile field, which is prone to contamination by various means other than the covered surgical system.

Minimally invasive surgery can be performed by inserting surgical instruments through orifices in a patient's body (e.g., natural orifices or body-wall incisions) and controlling the surgical instruments via an interface on the outside of the body. In various embodiments of the present disclosure, the surgical instruments are teleoperated by surgeons. Thus, the surgeons do not move the instruments by direct physical contact, but instead control instrument motion from some distance away by moving master controllers ("masters"). The operating surgeon is typically provided with a view of the actual surgical site via a visual display, so that the surgeon may remotely perform surgical motions on the masters while viewing the surgical site. A controller of the surgical system causes the surgical instrument to be moved in accordance with movement of the masters.

Figure 1:
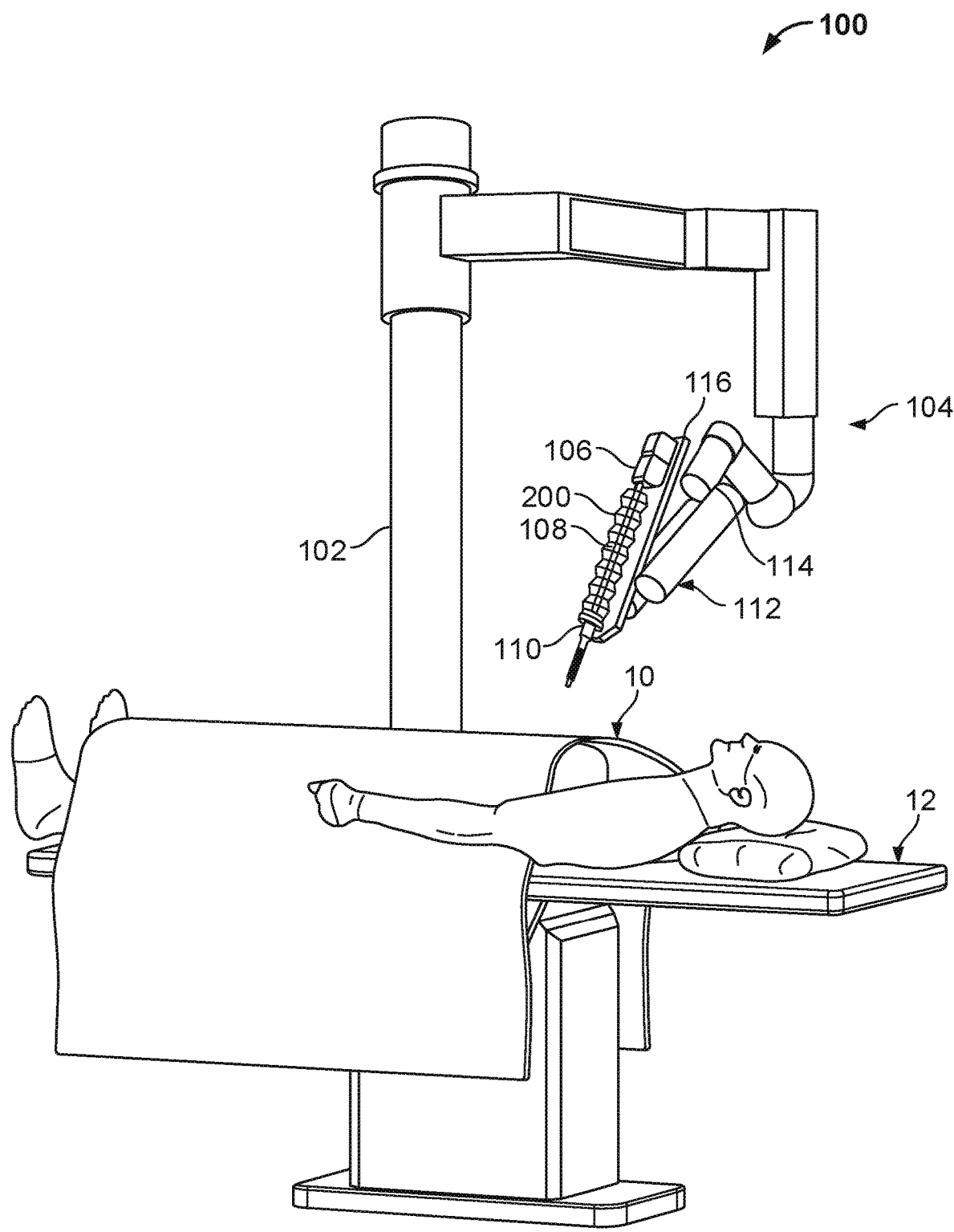
FIG. 1 is a perspective view of a portion of a teleoperated surgical system.

FIG. 1 depicts a patient-side portion 100 of a teleoperated surgical system in accordance with one or more embodiments of the present invention. Patient-side portion 100 is a robotic system for performing minimally invasive surgery on a patient's body 10 positioned on an operating table 12. Patient-side portion 100 includes a column 102, a support assembly 104, and an instrument carriage 106. In this example, column 102 anchors patient-side portion 100 on a floor surface (not shown) proximate operating table 12. However, in other embodiments the patient-side portion may be mounted to a wall, to the ceiling, to the operating table supporting the patient's body, or to other operating room equipment. Support assembly 104 branches radially outward from the trunk, and instrument carriage 106 resides at a distal end of the support assembly. Instrument carriage 106 supports a detachable surgical instrument 108, and it includes various actuators and control connections for controlling functionality of the instrument during a surgical procedure within the patient's body 10. In particular, the teleoperated actuators housed in instrument carriage 106 provide a number of controller motions that surgical instrument 108 translates into a corresponding variety of movements of the instrument's end effector. An entry guide 110 (e.g., a cannula) serves as a surgical port to an orifice of the patient's body 10 that receives surgical instrument 108 to guide the instrument into the patient. Entry guide 110 may perform various other functions, such as allowing fluids and other materials to pass into or out of the body, and reducing trauma at the surgical site by isolating at least some motion (e.g., translating movement along an insertion axis and axial rotation of the instrument shaft) of the surgical instrument from the body wall.

The term "surgical instrument" is used herein to describe a medical device for insertion into a patient's body and use in performing surgical or diagnostic procedures. A surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components. Surgical instruments appropriate for use in one or more embodiments of the present disclosure may control their end effectors (surgical tools) with one or more rods and/or flexible cables. In some examples, rods, which may be in the form of tubes, may be combined with cables to provide a "push/pull" control of the end effector, with the cables providing flexible sections as required. A typical elongate shaft for a surgical instrument is small, perhaps five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The rods and cables must fit within the elongate shaft and be able to control the end effector through the wrist joint.

Support assembly 104 further includes an instrument manipulator 112 that controls positioning of surgical instrument 108 relative to the patient's body 10. In various implementations, instrument manipulator 112 may be provided in a variety of forms that allow surgical instrument 108 to move with one or more mechanical degrees of freedom (e.g., all six Cartesian degrees of freedom, five or fewer Cartesian degrees of freedom, etc.). Typically, mechanical or control constraints restrict instrument manipulator 112 to move surgical instrument 108 around a particular center of motion that stays stationary with reference to the patient's body 10. This center of motion is typically located proximate where surgical instrument 108 enters the patient's body 10 (e.g., at some point along entry guide 110, such as the midpoint of the body wall). In this example, instrument manipulator 112 includes a joint 114 and an elongated spar 116 supporting instrument carriage 106 and entry guide 110. In this example, instrument carriage 106 is mounted to ride along the length of spar 116 while entry guide 110 is held fixed, so as to translate surgical instrument 108 through the entry guide along an insertion axis relative to the patient's body 10. Adjusting joint 114 locates surgical instrument 108 at a desired angular orientation about the center of motion, while movement of carriage 106 along spar 116 locates the surgical instrument at a desired insertion point through the center of motion. Thus, the teleoperated actuators of instrument manipulator 112 move surgical instrument 108 as a whole, as compared to the teleoperated actuators housed in instrument carriage 106, which move only the instrument's end effector or other individual instrument components. Manipulator 112 as shown is illustrative of both manipulators that are configured to constrain the remote center of motion by fixed intersecting manipulator joint axes (hardware-constrained remote center of motion) and manipulators controlled by software to keep a defined remote center of motion fixed in space (software-constrained remote center of motion).

Figure 2A:
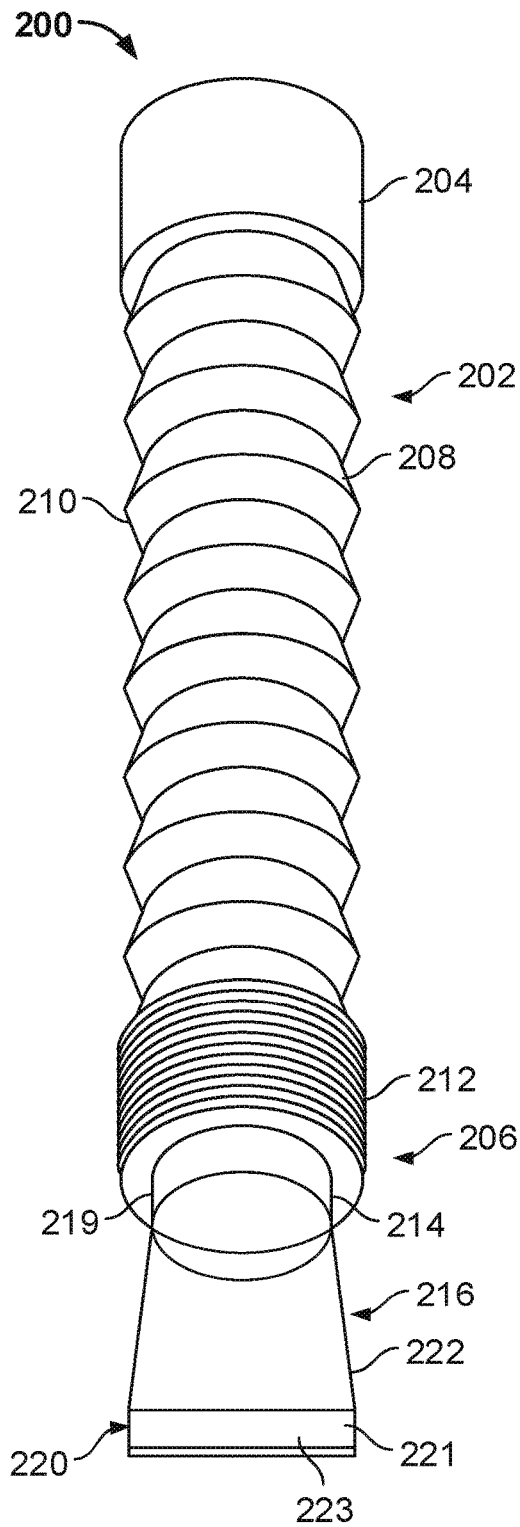
FIG. 2A is side view of a first example instrument drape.

As shown in FIG. 2A, surgical drape 200 providing a localized sterility barrier about surgical instrument 108 extends along the shaft of the instrument between instrument carriage 106 and entry guide 110. Surgical drape 200 includes a hollow tube 202, a base coupler 204 at a proximal end of the tube, and a port coupler 206 at a distal end of the tube. In this description, proximal means farther away from the surgical site, and distal means closer to the surgical site. In some examples, each of these components is formed from a suitable plastic material (e.g., thermoplastic polyurethane), or any other material capable of withstanding a sterilization process. As such, in some implementations of surgical drape 200 may be re-used over multiple surgical procedures following sterilizations together with, or apart from, surgical instrument 108 (e.g., autoclaving). In other implementations, however, surgical drape 200 is constructed to be sterilized for a single use (e.g., by gamma irradiation), and is not intended to be sterilized for reuse. Alternatively, drape 200 may be configured for reuse by using commonly known disinfection agents.

Figure 3:
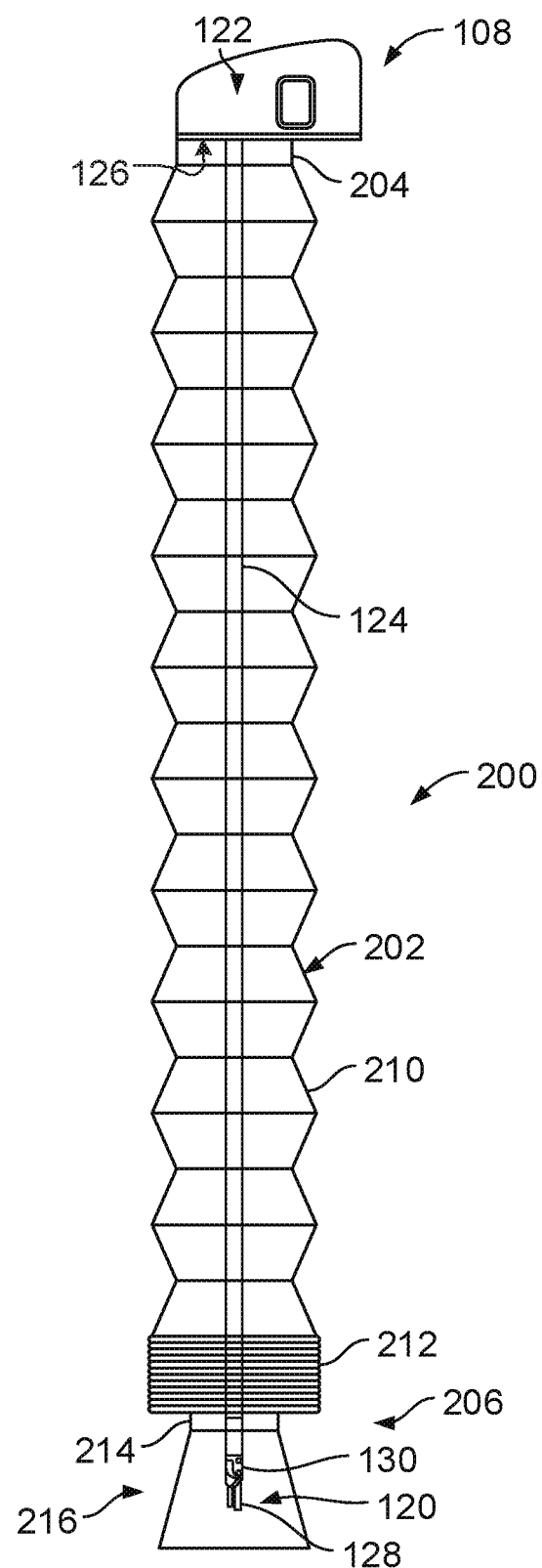
FIG. 3 is a side view of a surgical instrument carrying the instrument drape of FIG. 2A.

FIG. 3 illustrates surgical drape 200 installed on surgical instrument 108. In this example, surgical instrument 108 includes a distal portion 120 and a proximal control mechanism 122 coupled by an elongate shaft 124. Proximal control mechanism 122 includes an instrument control surface 126 that provides connections to the control features of surgical instrument 108. Instrument control surface 126 couples to instrument carriage 106, which controls surgical instrument 108, as discussed above. Distal portion 120 of surgical instrument 108 may provide any of a variety of surgical tools, such as the forceps 128 shown, a needle driver, a cautery device, a cutting tool, an imaging device (e.g., an endoscope or ultrasound probe), or a combined device that includes a combination of two or more various tools and imaging devices. Further, in the illustrated embodiment, forceps 128 are coupled to elongate shaft 124 by a wrist joint 130, which allows the orientation of the forceps to be manipulated with reference to the elongate shaft 124.

In addition, as shown in FIG. 3, in some implementations the drape is long enough so that it extends from the base of the instrument past the end effector. This feature allows end effector to remain inside the drape when the instrument is removed from the instrument carriage with the drape attached. Thus the instrument with the attached drape can be placed on a non-sterile surface, but the end effector and shaft remain sterile for reinsertion into the patient if the instrument is once again mounted on the instrument shaft.

Referring to FIGS. 2A and 3, tube 202 includes an impervious tubular wall 208 defining an interior bore appropriately sized to receive the elongated shaft of surgical instrument 108. The interior surface of tubular wall 208 exposed to surgical instrument 108 is sterile, while the exterior surface is optionally non-sterile. Tube 202 is a readily collapsible along its length in order to accommodate relative movement between surgical instrument 108 and entry guide 110 via movement of instrument carriage 106 along spar 116. In this example, tube 202 is provided in the form of an accordion structure including a series of accordion folds 210 distributed along its length. Thus, tube 202 is configured to reversibly collapse by compressing accordion folds 210 as instrument 108 is inserted into the patient's body 10 along the insertion axis. Providing accordion folds 210 to facilitate the reversible collapse of tube 202 allows the material of the tube to be (optionally) somewhat stiff. For example, tube 202 may be sufficiently stuff to inhibit distention by an insufflation gas released into the tube through entry guide 110.

Base coupler 204 is at the proximal end, and port coupler 206 is at the distal end of tube 202. Base coupler 204 is configured to couple the proximal end of tube 202 to a proximal base of surgical instrument 108. In this example, base coupler 204 is provided in the form of an internally threaded screw-on adapter that releasably engages a corresponding pattern of external threads formed at the base of elongate shaft 124 just below proximal control mechanism 122. The attachment between the mating screw threads of base coupler 204 and elongate shaft 124 provides a fluid-tight, sealed sterile connection to prevent contamination of the inverted sterile field within tube 202. One or more gaskets or o-ring seals may be used to facilitate the fluid-tight connection. Notably, in some alternative embodiments, the surgical drape may be secured to the surgical instrument by a different configuration of structural elements, such that the drape is not directly connected to the instrument shaft. For example, a portion of the surgical drape may be attached to the base of the instrument (e.g., at or near the proximal control mechanism), which, unlike the shaft on certain instruments, is rotationally fixed with respect to the entry guide. This configuration relaxes the requirements on the torsional stiffness of the drape, and it mitigates the risk of corrupting any proximal force-sensing measurements that take place in the instrument base.

Port coupler 206 is configured to couple the distal end of tube 202 to entry guide 110, through which the shaft of surgical instrument 108 extends. In this example, port coupler 206 includes a handling ring 212, a collar 214, and a closure member 216. Handling ring 212 is a cylindrical member directly attached to the distal end of tube 202, and it is appropriately sized to be readily grasped and manipulated by a human hand. Handling ring 212 is provided so that a user can quickly and easily create a fluid-tight, sealed, sterile connection between port coupler 206 and entry guide 110 to establish the sterile field within tube 202, as discussed below. Closure member 216 is a self-sealing structure configured to automatically (i.e., without user intervention) seal the interior bore of tube 202 when port coupler 206 is detached from entry guide 110. In this example, closure member 216 includes an open cylindrical base 219 extending from collar 214 towards a self-sealing element 220. In this example, self-sealing element 220 includes opposing lips 221 coupled to one another by respective hinges 222. Self-sealing element 220 is configured to reversibly transition from a closed condition shown in FIG. 2A and an opened condition in response to a sufficient external force. The closed condition is the natural, unstressed state of the self-sealing element. In the closed condition, where lips 221 are held against one another, self-sealing element 220 provides a fluid-tight seal inhibiting (if not entirely preventing) fluid ingress or egress to and from the sterile field within the bore of tube 202. In the opened condition, where lips 221 are parted from one another, self-sealing element 220 permits uninhibited fluid flow through the distal end of tube 202. (An example of this configuration is a "duck bill" type single-slit seal or cross-slit seal.) Thus, insufflation gas from the body cavity may be released into the bore of tube 202 via entry guide 110 during a surgical procedure. The sealed connections provided by the base and port couplers inhibit leaking of insufflation gas to the surrounding environment.

In some examples, the above-described functionality of self-sealing element 220 is enabled by optionally forming this portion of closure member 216 as a substantially rigid and resilient structure that effectively resists external flexure forces urging the closure to the opened condition and promptly recovers from deformation to the closed condition when the external force is removed. In some examples, the self-sealing functionality is enabled by optionally providing a magnetic component 223 along a portion of lips 221. For instance, magnetic component 223 may include opposing magnetic strips or magnetic ink bonded to the interior surface of lips 221, such that the magnetic attraction of the strips or ink urges the lips of the closure together into the closed condition.

Figure 2C:
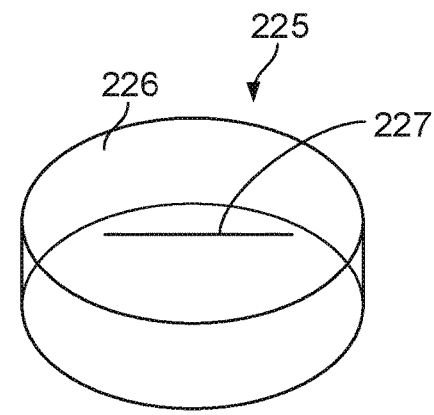
FIG. 2C is a side view of an adapter cap for facilitating a sterile connection between the instrument drape and drape adapter of FIGS. 2A and 2B.
Figure 2B:
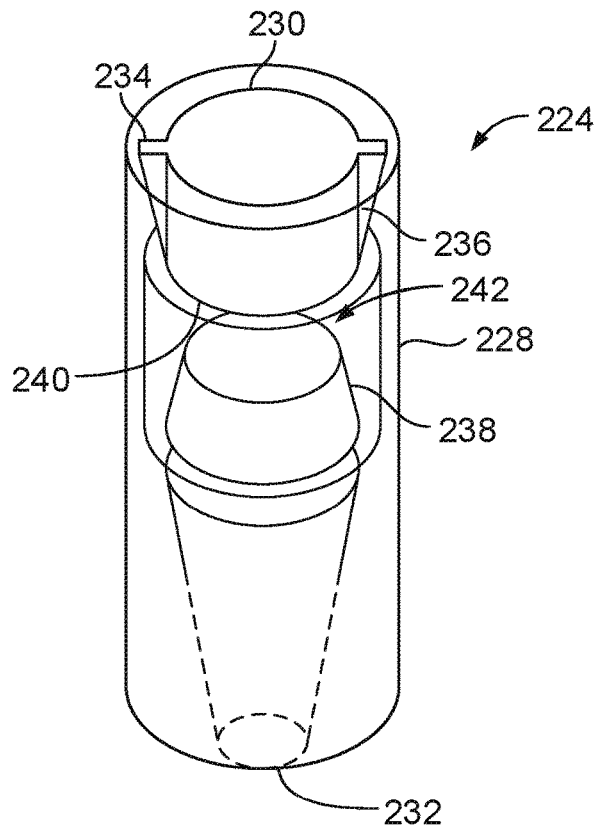
FIG. 2B is a side view of a drape adapter for receiving a portion of the instrument drape of FIG. 2A.

Referring next to FIGS. 2B and 2C, an adapter 224 and an adapter cap 225 are provided to facilitate the sealed connection between port coupler 206 and entry guide 110. In some examples, adapter 224 and adapter cap 225 are incorporated as an assembly with entry guide 110, or they are attached to the entry guide during setup procedures. Adapter 224 includes a tubular body 228 defining an interior bore extending from a proximal opening 230 to a distal opening 232. Adapter cap 225 fits over the top of tubular body 228, such that a flexible membrane 226 of the cap covers the tubular body's proximal opening 230. A slit 227 in flexible membrane 226 is configured to receive self-sealing element 220 and maintain a sterile seal with closure member 216.

Adapter 224 further includes a plurality of structural elements residing within its interior bore. These structural elements are configured to interface with port coupler 206 to form a sealed connection. In this example, adapter 224 includes a seal guide 234, a reduction cone 236, and an accepting cone 238. Seal guide 234 includes a pair of radial notches diametrically opposed to one another along the circumference of proximal opening 230. Together with proximal opening 230, seal guide 234 provides a radial slot for receiving self-sealing element 220 in the substantially flat, closed condition shown in FIG. 2A. Reduction cone 236 includes a pair of grooves leading axially and inwardly from the radial notches of seal guide 234. The grooves of reduction cone 236 taper inward towards the center of tubular body 228 and provide a gradually reduced diameter compared to proximal opening 230. During use, the closed self-sealing element 220 is aligned with seal guide 234, and pressed into reduction cone 236. As self-sealing element 220 traverses reduction cone 236, the inwardly projecting grooves press against the element's hinges 222 to force opposing lips 221 apart from one another. The now partially opened self-sealing element 220 is pushed through an interior reduced-diameter opening 240 and introduced to a sterile gap 242 surrounding accepting cone 238. As self-sealing element 220 continues to traverse the interior bore of tubular body 228, the opening between parted lips 221 receives accepting cone 238. Accepting cone 238 is a hollow, frustum shaped structure having a tubular wall that tapers radially outward along its length. Thus, as self-sealing element 220 is pushed even further through tubular body 228, the hinged lips 221 bear against the outwardly extending wall of accepting cone 238, which maintains the self-sealing element in the opened condition. In some examples, lips 221 can become wedged against the outer wall of accepting cone 238 and/or the interior wall of the bore of the tubular body to form a fluid-tight seal. With self-sealing element 220 held open, surgical instrument 108 can traverse the sealed connection(s) between port coupler 206 and entry guide 110 to enter the body cavity. Other receiving configurations may be used, depending on the self-sealing element's shape.

Figure 4A:
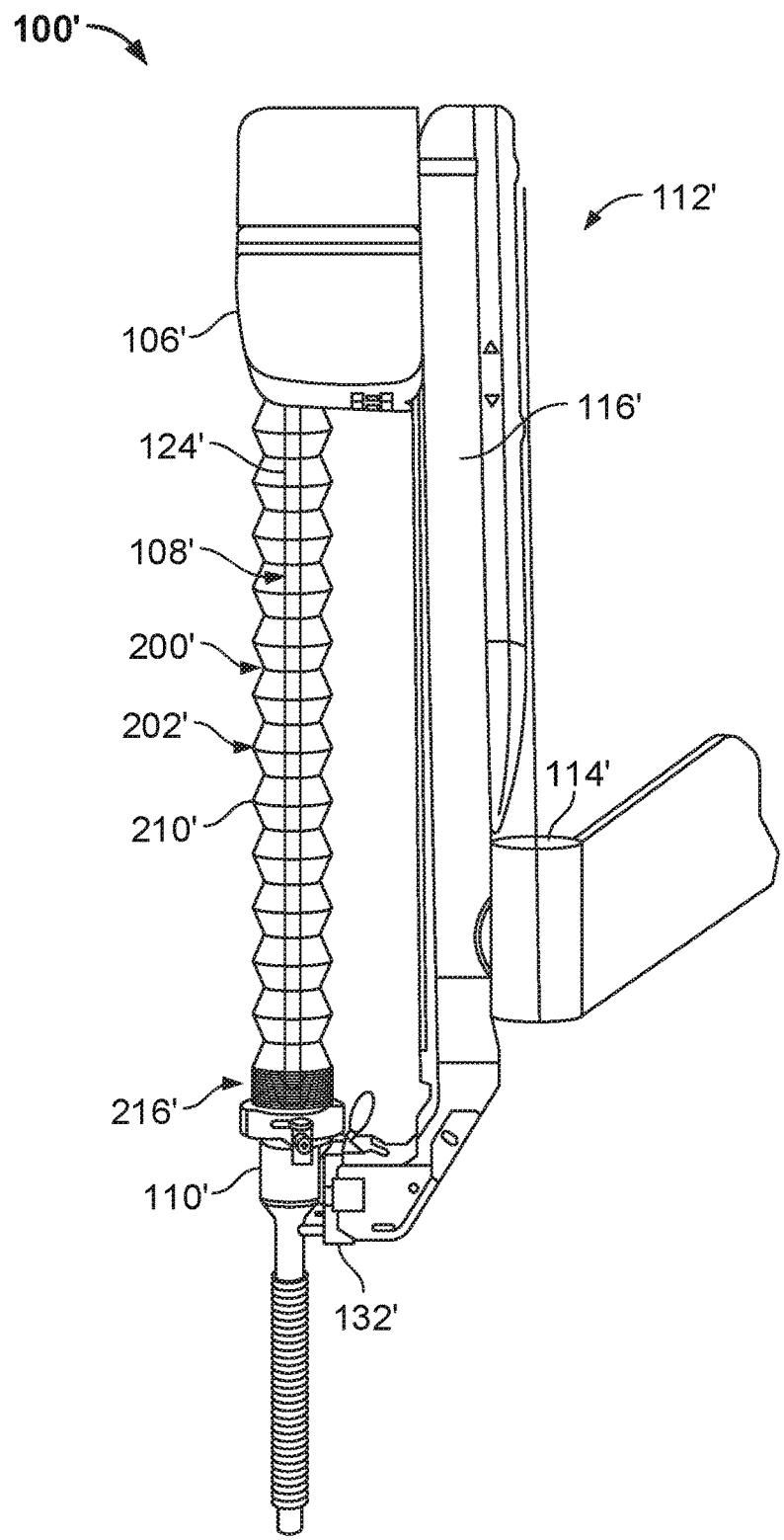
FIG. 4A is a side view of a portion of a surgical manipulator positioning the surgical instrument of FIG. 3 in a raised position.
Figure 4B:
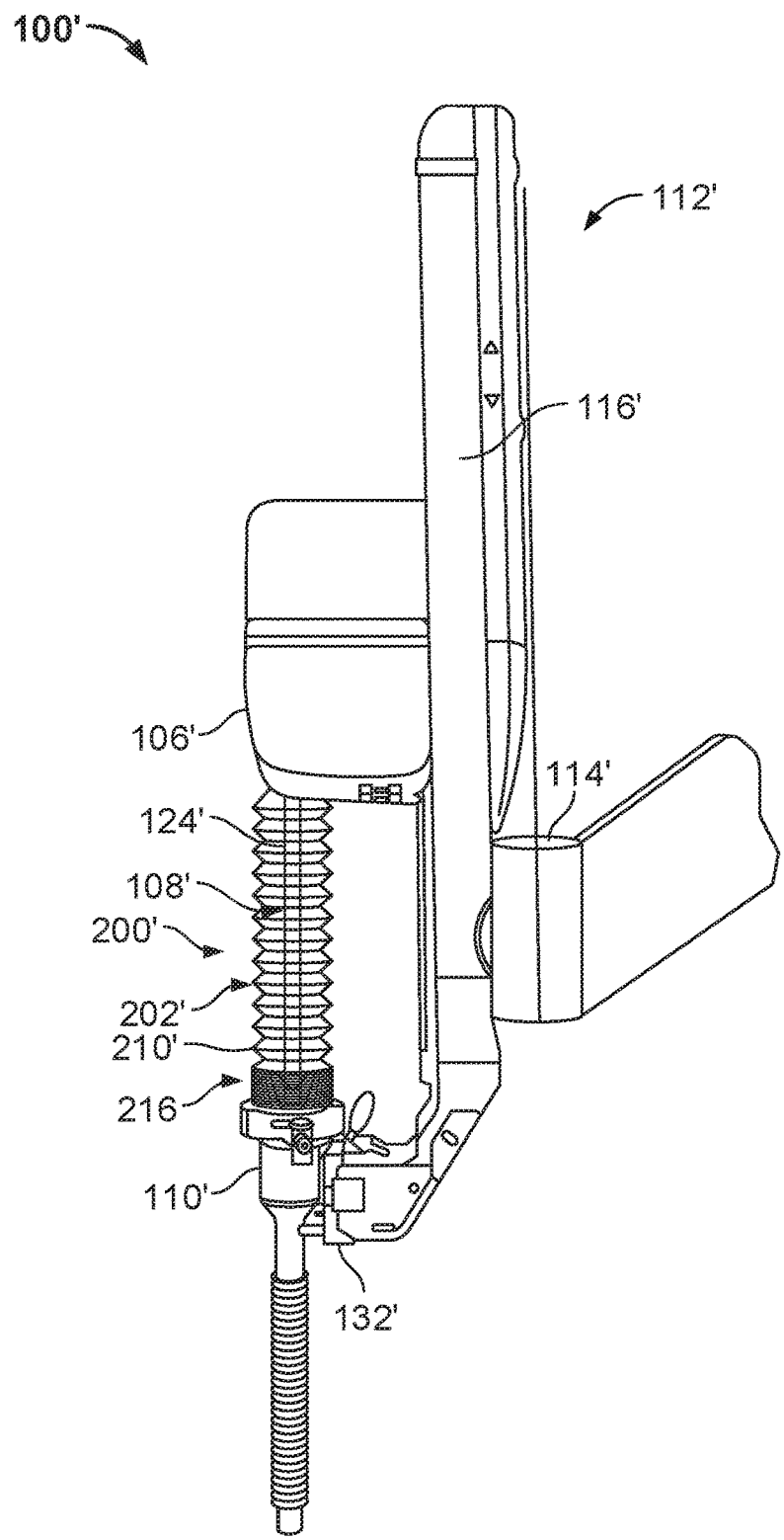
FIG. 4B is a side view of a portion of a surgical manipulator positioning the surgical instrument of FIG. 3 in a lowered position.

Referring next to FIGS. 4A and 4B, patient-side portion 100' includes manipulator 112' including spar 116' supporting instrument carriage 106' and entry guide 110'. Spar 116' is coupled to an adjustable joint 114' configured, in this example, to facilitate roll motion of the spar (of course, however, various other joint configurations could also be used). Instrument carriage 106' is movable along the length of spar 116' and entry guide 110' is held in a fixed position by a connector 132' at the distal end of the spar. Surgical drape 200' is installed on surgical instrument 108', and defines an inverted sterile field along the length of shaft 124 between instrument carriage 106' and entry guide 110'. The proximal control mechanism 122' of surgical instrument 108' is mounted to instrument carriage 106', and the elongate shaft 124' of the instrument extends down through entry guide 110'. Entry guide 110' may include a suitable adapter (e.g., adapter 224 and/or adapter cap 225) for facilitating a sealed connection between a port coupler 206' of surgical drape 200' and entry guide 110'. Further, as discussed above with reference to FIG. 2A, surgical drape 200' includes a tube 202' having compressible accordion folds 210' that permit the tube to reversibly collapse along its length as instrument carriage 106' is moved downward towards entry guide 110' in order to insert surgical instrument 108 further into the body cavity. Thus, during use, surgical drape 200' is manipulated from the first state shown in FIG. 4A, where accordion tube 202' is extended with instrument carriage 106' in a raised (proximal) position of spar 116', to the second state shown in FIG. 4B, where accordion tube 202' is collapsed with instrument carriage 106' in a lowered (distal) position on spar 116'.

Figure 5:
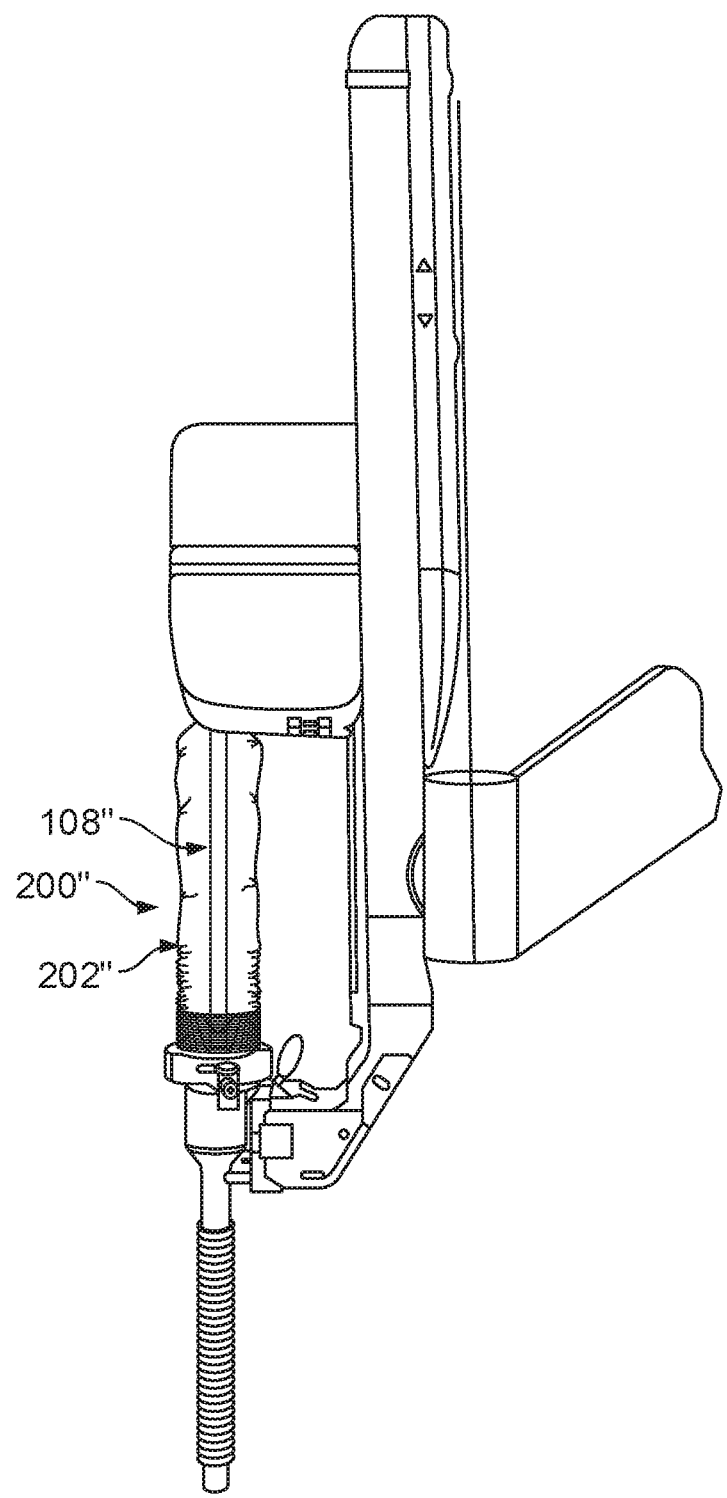
FIG. 5 is a side view of a portion of a surgical manipulator positioning a surgical instrument carrying a second example instrument drape in a lowered position.

FIG. 5 illustrates a similar example involving a surgical drape 200" having a collapsible tube 202" forming an inverted sterile field about the shaft of surgical instrument 108." In this example, however, tube 202" includes a thin sheet of film sufficiently flexible to facilitate the reversible collapsing functionality, in lieu of the accordion folds shown in the embodiment of FIGS. 4A and 4B. In some examples, a lubricant may be applied to the outer surface of tube 202" to reduce the tackiness of the material as it collapses on itself.

A method of configuring a robotically operable surgical instrument (e.g., instrument 108) for a surgical procedure may include the steps of: attaching a first end of a surgical drape to a proximal base of the surgical instrument, positioning an elongated tubular portion of the drape to cover the instrument shaft, and attaching a second end of the drape to an entry guide serving as a surgical port to the patient's body. Thus, the surgical drape forms a sterility barrier extending along the instrument shaft between the proximal base and the entry guide. The sterility barrier is deformable as the instrument is advance into the body cavity through the entry guide. In some examples, the first end of the drape is provided in the form of a base coupler including an internally threaded screw-on adapter mating with external screw threads (or other suitable attachment means) formed on the outer surface of the instrument shaft. In some examples, the second end of the drape is provided in the form of a port coupler configured to form a sterile seal with an adapter of the entry guide. The port coupler may include a self-sealing element that maintains the sterile integrity of the drape when it is detached from the entry guide. This self-sealing functionality allows the surgical instrument to be removed from the supporting manipulator and re-used during a surgical procedure.

In the above description, numerous specific details are set forth. However, it is understood that embodiments of the invention may be practiced without these specific details. In other instances, well-known circuits, structures, and techniques have not been shown in detail in order not to obscure the understanding of this description. In the above description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The above detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "below", "lowered", "raised", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

What is claimed is:

1. A surgical drape comprising:
    a tube having a proximal end and a distal end, the tube defining an interior bore sized to receive an elongated shaft of a surgical instrument;
    a port coupler at the distal end of the tube, the port coupler comprising:
        a handling portion configured to be grasped and manipulated by a human hand to engage the port coupler with an entry guide through a sealed sterile connection, the entry guide comprising a cannula that defines a surgical port through which the elongated shaft extends; and
        a sealed closure configured to open in response to a force exerted by a surface of the entry guide; and
    a base coupler at the proximal end of the tube, the base coupler comprising a fastener releasably engageable with a mating fastener of the surgical instrument at a proximal portion of the shaft; and
    wherein the tube is collapsible to accommodate relative movement between the instrument and the surgical port.

2. The surgical drape of claim 1, wherein the tube comprises a sheet of film sufficiently flexible to reversibly collapse as the proximal portion of the shaft is moved relative to the surgical port.

3. The surgical drape of claim 1, wherein the tube comprises an accordion structure configured to reversibly collapse as the proximal portion of the shaft is moved relative to the surgical port.

4. The surgical drape of claim 1, wherein the base coupler, tube, and port coupler are configured to withstand a sterilization process.

5. The surgical drape of claim 1, wherein the tube comprises an impervious tube wall having an exterior surface and a sterile interior surface.

6. The surgical drape of claim 1, wherein the port coupler is configured to form a sterile seal with the surgical port.

7. The surgical drape of claim 1, wherein the sealed closure of the port coupler comprises a self-sealing closure configured to seal the interior bore of the tube when the port coupler is detached from the surgical port.

8. The surgical drape of claim 7, wherein the self-sealing closure comprises a resilient sealing lip, the sealing lip comprises a pair of opposing hinges configured to facilitate opening of the self-sealing closure.

9. The surgical drape of claim 7, wherein the self-sealing closure comprises a magnetic element along a portion of the distal end of the tube.

10. The surgical drape of claim 1, wherein the tube encloses the shaft within a sterile field along a length of the shaft extending from a control mechanism coupled at the proximal portion of the shaft to the surgical port.

11. The surgical drape of claim 10, wherein the length comprises an entire exposed length of the shaft.

12. The surgical drape of claim 10, wherein the mating fastener is located on the control mechanism.

13. A surgical drape comprising:
- a tube having a proximal end and a distal end, the tube defining an interior bore sized to receive an elongated shaft of a surgical instrument mounted to move along a spar of a robotic surgical system;
- a port coupler at the distal end of the tube, the port coupler comprising:
  - a handling portion configured to be grasped and manipulated by a human hand to engage the port coupler with an entry guide through a sealed sterile connection, the entry guide fixed to the spar and comprising a cannula that defines a surgical port through which the elongated shaft extends; and
  - a sealed closure configured to open in response to a force exerted by a surface of the entry guide;
- wherein the tube is collapsible to accommodate relative movement between the instrument and the surgical port,
- a base coupler at the proximal end of the tube, the base coupler configured to couple the tube to a proximal base of the instrument,
- wherein the tube comprises an accordion structure configured to reversibly collapse as the proximal base is moved relative to the surgical port, and
- wherein the tube is sufficiently stiff to inhibit distention by an insufflation gas released through the surgical port into the tube.

* * * * *